United States Patent
Kremsl et al.

(10) Patent No.: US 9,986,976 B2
(45) Date of Patent: Jun. 5, 2018

(54) METHOD AND SYSTEM FOR DYNAMICALLY CHANGING AN IMPEDANCE OF A TRANSMIT/RECEIVE SWITCH

(71) Applicant: General Electric Company, Schenectady, NY (US)

(72) Inventors: Andreas Kremsl, Zipf (AT); Reinhold Bruestle, Zipf (AT); Erwin Fosodeder, Zipf (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 828 days.

(21) Appl. No.: 14/584,191

(22) Filed: Dec. 29, 2014

(65) Prior Publication Data
US 2016/0183927 A1    Jun. 30, 2016

(51) Int. Cl.
*A61B 8/00* (2006.01)
*A61B 8/14* (2006.01)
*A61B 8/08* (2006.01)
*G01S 7/52* (2006.01)

(52) U.S. Cl.
CPC .......... *A61B 8/5269* (2013.01); *G01S 7/5208* (2013.01); *A61B 8/4444* (2013.01)

(58) Field of Classification Search
CPC .... A61B 8/5269; A61B 8/4444; G01S 7/5208
See application file for complete search history.

(56) References Cited

U.S. PATENT DOCUMENTS

| 4,486,867 A * | 12/1984 | Hill ........................... G01S 7/52 |
| | | 200/61.02 |
| 7,139,532 B2 | 11/2006 | Veillette |
| 2016/0183927 A1* | 6/2016 | Kremsl ................ A61B 8/5269 |
| | | 600/443 |
| 2016/0209481 A1* | 7/2016 | Gunamony ........ G01R 33/3415 |

* cited by examiner

*Primary Examiner* — Daniel Pihulic
(74) *Attorney, Agent, or Firm* — McAndrews, Held & Malloy, Ltd.; Jacob Groethe; David Bates

(57) ABSTRACT

Various embodiments include a system and method that enhance performance of an ultrasound system by dynamically changing an impedance of a transmit/receive switch. The system can include a transmit/receive switch and a low noise amplifier. The transmit/receive switch may be configured to switch between a transmit phase and a receive phase of an ultrasound scan. The transmit/receive switch may provide a receive signal communicated from an ultrasound transducer to a low noise amplifier when in the receive phase. An impedance of the transmit/receive switch may be dynamically adjusted by changing a resistance of the transmit/receive switch while the transmit/receive switch is in the receive phase. The low noise amplifier may be configured to amplify the receive signal. In various embodiments, a gain of the low noise amplifier is independent of the resistance of the transmit/receive switch.

20 Claims, 7 Drawing Sheets

METHOD AND SYSTEM FOR DYNAMICALLY CHANGING AN IMPEDANCE OF A TRANSMIT/RECEIVE SWITCH

CROSS-REFERENCE TO RELATED APPLICATIONS/INCORPORATION BY REFERENCE

[Not Applicable]

FIELD OF THE INVENTION

Certain embodiments of the invention relate to transmit/receive switches in a frontend of an ultrasound system. More specifically, certain embodiments of the invention relate to a method and system for enhancing performance of an ultrasound system by dynamically changing an impedance of a transmit/receive switch.

BACKGROUND OF THE INVENTION

A transmit/receive switch is commonly used within a frontend of an ultrasound system to switch between a transmit phase and a receive phase of an ultrasound scan. The transmit/receive switch allows the transducer elements of the ultrasound system to be used for both the transmit phase and the receive phase. The switch may provide protection for the receiver electronics from the high voltage signals used during the transmit phase.

In transmit/receive switch arrangements, an electrical load at the transducer elements during the receive phase is mainly provided by the resistance of the closed switch and the input impedance of a subsequent low noise amplifier. An impedance ratio between the transducer elements and the combination of the closed switch and low noise amplifier influences the performance of the ultrasound system. For example, reverberation artifacts may be minimized by matching the impedance of the transducer with the impedance of the combination of the closed switch and low noise amplifier. The minimization of the reverberation artifacts can be important, for example, at a depth of a few centimeters during an ultrasound examination of a pregnant uterus, i.e., at the amniotic fluid.

Existing transmit/receive switch and low noise amplifier arrangements that provide control of a switch resistance may not be desirable because the gain of the low noise amplifier varies with the adjustment of the switch resistance. Further, existing transmit/receive switch arrangements that adjust a switch resistance to match the impedance at the transducer may not adequately reduce the input signal level into the low noise amplifier in the near field, when the receive voltage level is high, to overcome saturation effects of the low noise amplifier. Existing transmit/receive switch arrangements that adjust a switch resistance to match the impedance at the transducer may also not consider the noise floor in the far field. For example, the switch resistance control of existing systems can be inadequate for setting the impedance of the transmit/receive switch to a low value to minimize the noise floor.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for enhancing performance of an ultrasound system by dynamically changing an impedance of a transmit/receive switch, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
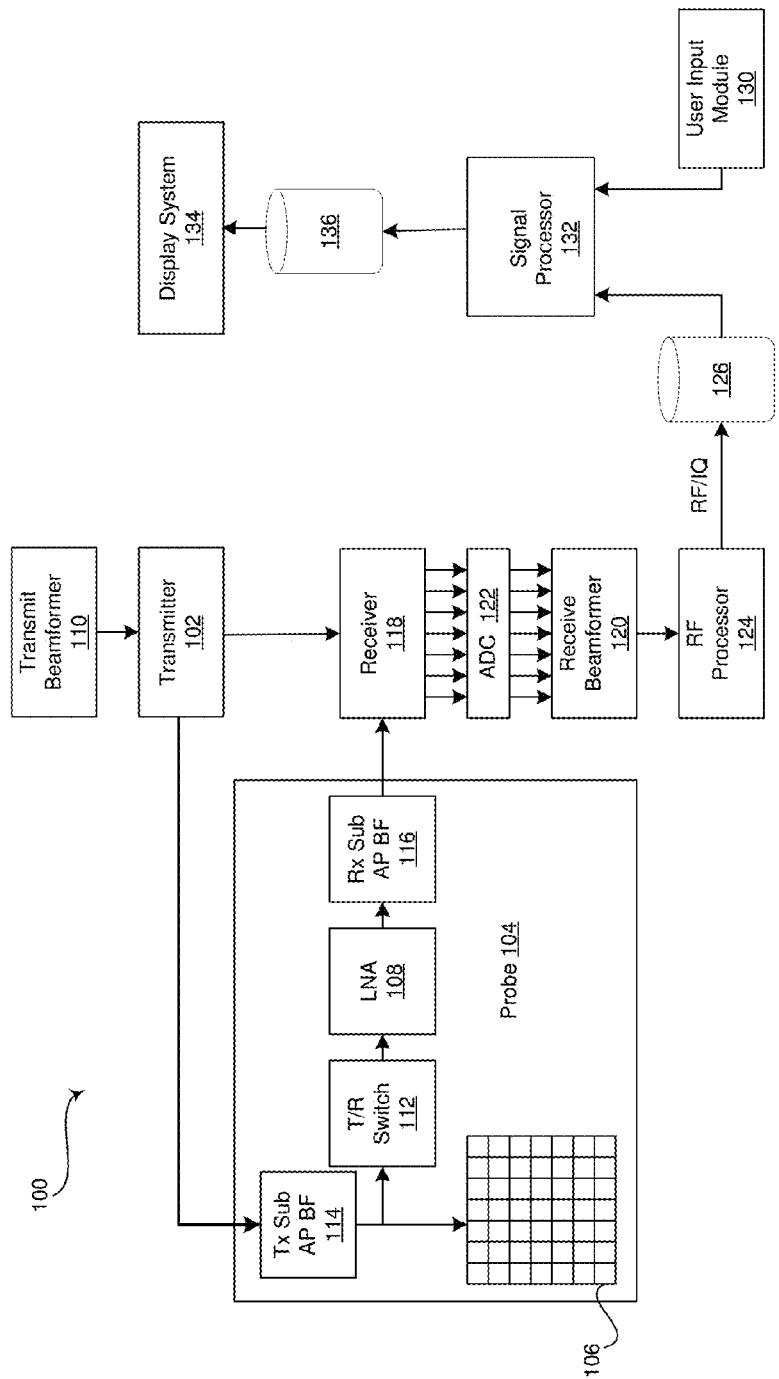
FIG. 1 is a block diagram of an exemplary ultrasound system that is operable to dynamically change an impedance of a transmit/receive switch, in accordance with an embodiment of the invention.

Certain embodiments of the invention may be found in a method 200 and system for enhancing performance of an ultrasound system 100 by dynamically changing an impedance of a transmit/receive switch 112. For example, aspects of the present invention have the technical effect of overcoming saturation effects of a low noise amplifier 108 by setting an impedance of a transmit/receive switch 112 to reduce the input signal level into the low noise amplifier 108 in the near field (e.g., when the receive voltage level is high).

As another example, aspects of the present invention have the technical effect of reducing reverberation artifacts by dynamically changing the impedance of the transmit/receive switch 112. The impedance of the transmit/receive switch 112 may be dynamically changed such that the impedance of the transducer 106 matches the impedance of the combination of the transmit/receive switch 112 and the low noise amplifier 108 input. The matched impedance minimizes the reflectivity of the transducer 106 at a depth of a few centimeters (e.g., at the amniotic fluid), thereby enhancing visualization of the corresponding ultrasound image or volume data.

Further, aspects of the present invention have the technical effect of minimizing a noise floor in the far field by reducing the impedance of the transmit/receive switch 112.

Various embodiments may provide the above-described technical effects by, for example, dynamically decreasing a variable part 116 of the transmit/receive switch 112 over depth when the variable part 116 is connected in series between a high voltage switch 114 and an input of a low noise amplifier 108. Certain embodiments may provide one or more of the above-described technical effects by, for example, increasing a variable part 116 of the transmit/ receive switch 112 over depth when the variable part 116 is connected in parallel between the input of the low noise amplifier 108 and ground. The switch resistance of the variable part 116 of the transmit/receive switch 112, irrespective of whether arranged in serial or parallel, is independent of the input resistance of the low noise amplifier 108. In other words, a gain of the low noise amplifier 108 is unaffected by the variable resistance 116 of the transmit/ receive switch 112.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to dynamically change an impedance of a transmit/receive switch 112, in accordance with an embodiment of the invention. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a one dimensional (1D, 1.25D, 1.5D or 1.75D) array or a two dimensional (2D) array of piezoelectric elements. The ultrasound probe 104 may comprise a group of transducer elements 106 that emit ultrasonic transmit signals into, and receive echoes from, a region of interest (e.g., human, animal, underground cavity, physical structure and the like). The ultrasound probe 104 may comprise a transmit/receive switch 112, a low noise amplifier 108, and transmit 114 and receive 116 sub-aperture beamformers.

The transmit beamformer 110 may comprise suitable logic, circuitry, interfaces and/or code that may be operable to control the transmitter 102 which, through a transmit sub-aperture beamformer 114 of the probe 104, drives the group of transmit transducer elements 106 to emit ultrasonic transmit signals. The transmitted ultrasonic signals may be back-scattered from structures in the object of interest, like blood cells or tissue, to produce echoes. The echoes are received by the transducer elements 106. The group of transducer elements 106 in the ultrasound probe 104 may be operable to convert the received echoes into analog signals. The analog signals are communicated to a receiver 118 by way of a transmit/receive switch 112, a low noise amplifier 108, and a receive sub-aperture beamformer 116.

The transmit/receive switch 112 may comprise suitable logic, circuitry, interfaces and/or code that may be operable to protect the low noise amplifier 108 from the high voltage transmit pulses and isolates the low noise amplifier input from the transmitter 102. The transmit/receive switch 112 is open during a transmit phase of an ultrasound scan and closed during the receive phase of the ultrasound scan, thereby passing only the low voltage signals received from the transducer elements 106. The transmit/receive switch 112 has a high recovery time to ensure that the receiver 118 is on immediately after a transmit pulse is discharged, such that the receiver 118 is able to process the signals communicated by the transducer elements 106, for example, at shallow depths when the transmit time of the acoustic wave beam is short. As discussed in further detail with reference to FIGS. 2-5 below, the transmit/receive switch 112 comprises a high voltage switch 114 having a fixed low impedance value and a second part 116 that is controlled to dynamically adjust the impedance of the transmit/receive switch 112 over time (i.e., at various depths of the acoustic signal within the region of interest). The second part 116 may comprise a low voltage transistor, which is either connected between the high voltage switch 114 and the low noise amplifier 108 input or after the high voltage switch 114 between the low noise amplifier 108 input and ground. The gate voltage of the second part 116 may be controllable over time in order to change the impedance of the transmit/receive switch 112 dynamically.

In various embodiments, an impedance ratio between the transducer 106 and the combination of the transmit/receive switch 112 and the low noise amplifier 108 influences the overall performance of the ultrasound system 100. For example, between the near and far fields, i.e., at a depth of a few centimeters, reverberation artifacts may be minimized by matching the impedance of the transducer 106 to the impedance of the transmit/receive switch 112 plus the low noise amplifier 108. Minimizing the reverberation artifacts at this depth, for example at the depth of the amniotic fluid in a pregnant uterus, enhances visualization of the amniotic fluid by reducing the reflectivity of the transducer 106.

The transmit/receive switch 112 is dynamically variable to enhance performance of the ultrasound system 100 in the near and far fields as well. For example, the receive voltage level may be higher in the near field of the receive phase. To overcome saturation effects of the low noise amplifier 108, the transmit/receive switch may be dynamically adjusted to have a higher impedance to reduce the input signal level into the low noise amplifier 108. In the far field, the impedance of the transmit/receive switch 112 may be adjusted as low as possible to minimize a noise floor of the low noise amplifier 108. Various embodiments dynamically reduce the transmit/receive switch 112 impedance over time as illustrated, for example, in FIG. 6. The output signal of the transmit/receive switch 112 passes through the low noise amplifier 108.

The low noise amplifier 108 may comprise suitable logic, circuitry, interfaces and/or code that may be operable to amplify the received low voltage signals from the transducer elements 106 during the receive phase while reducing the effect of noise. The low noise amplifier 108 is protected from high voltage signals used during a transmit phase of an ultrasound scan by the transmit/receive switch 112. The low noise amplifier 108 is designed based on noise performance and gain considerations. The signal amplified by the low noise amplifier 108 undergoes sub-aperture beamforming by a receive sub-aperture beamformer 116 and is subsequently communicated to the receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, change scan mode, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the transmit/receive switch 112, the low noise amplifier 108, the receiver 118, the receive beamformer 120, the RF processor 124, the RF/IQ buffer 126, the user input module 130, the signal processor 132, the image buffer 136, and/or the display system 134.

The signal processor 132 may comprise suitable logic, circuitry, interfaces and/or code that may be operable to process ultrasound scan data (i.e., RF signal data or IQ data pairs) for generating an ultrasound image for presentation on a display system 134. The signal processor 132 is operable to perform one or more processing operations according to a plurality of selectable ultrasound modalities on the acquired ultrasound scan data. In an exemplary embodiment of the invention, the signal processor 132 may be operable to perform compounding, motion tracking, and/or speckle tracking. Acquired ultrasound scan data may be processed in real-time during a scanning session as the echo signals 109 are received. Additionally or alternatively, the ultrasound scan data may be stored temporarily in the RF/IQ buffer 126 during a scanning session and processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds worth of frames of ultrasound scan data. The frames of ultrasound scan data are stored in a manner to facilitate retrieval thereof according to its order or time of acquisition. The image buffer 136 may be embodied as any known data storage medium.

In various embodiments, signal processor 132 may comprise suitable logic, circuitry, interfaces and/or code that may be operable to dynamically control the impedance of transmit/receive switch 112. For example, the signal processor 132 may provide control signals to change the variable resistance provided by variable resistor 116. The control signals may, for example, control a gate voltage of the variable resistor 116 over time to select the resistance provided by the variable resistor 116. The control signals may, for example, be predetermined or based on measured conditions, such as the impedance seen at the group of transducers 106, among other things.

Figure 2:
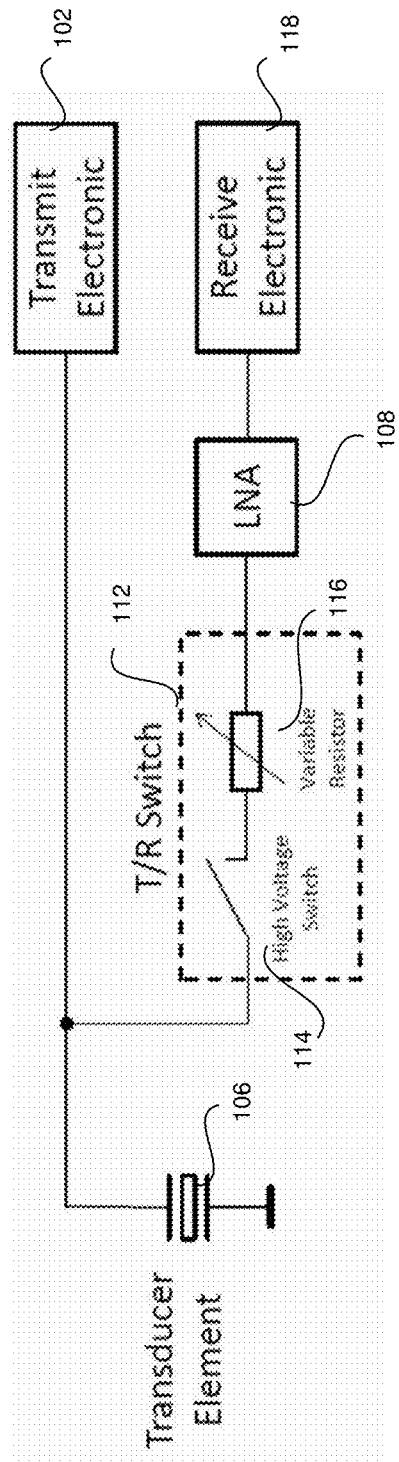
FIG. 2 is a block diagram of an exemplary frontend arrangement of an ultrasound system operable to enhance performance of the ultrasound system by dynamically changing an impedance of a transmit/receive switch, in accordance with an embodiment of the invention.

FIG. 2 is a block diagram of an exemplary frontend arrangement of an ultrasound system 100 operable to enhance performance of the ultrasound system 100 by dynamically changing an impedance of a transmit/receive switch 112, in accordance with an embodiment of the invention. Referring to FIG. 2, the frontend of the ultrasound system 100 comprises a transmitter 102, a receiver 118, a transducer 106, a transmit/receive switch 112, and a low noise amplifier 108. The transmitter 102 may be operable to drive a group of transducer elements 106 that emit ultrasonic transmit signals into, and receive echoes from, a region of interest. The group of transducer elements 106 in the ultrasound probe 104 may be operable to convert the received echoes into analog signals that are communicated to a receiver 118 via a transmit/receive switch 112 and a low noise amplifier 108.

Figure 4:
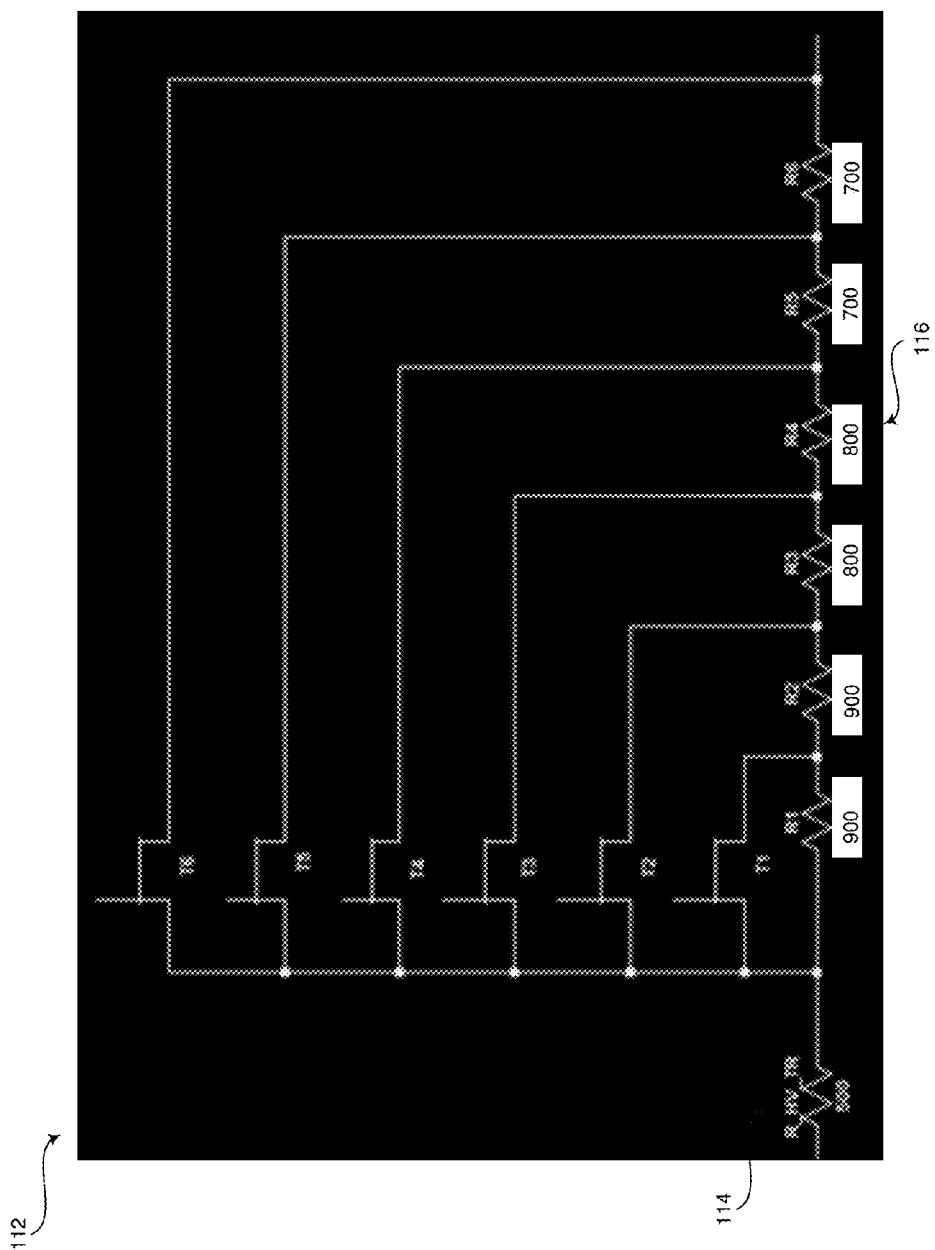
FIG. 4 is a diagram of first exemplary circuitry of the transmit/receive switch arrangement illustrated in FIG. 2 configured to dynamically change an impedance of the transmit/receive switch, in accordance with an embodiment of the invention.

The transmit/receive switch 112 comprises a high voltage switch 114 and a dynamically controlled variable resistor 116. The high voltage switch 114 may have a fixed low impedance value. The variable resistor 116 may be connected in series between the high voltage switch 114 and a low noise amplifier 108. The variable resistor 116 may be configured to change the impedance of the transmit/receive switch 112 over time. FIG. 4 is a diagram of first exemplary circuitry of the transmit/receive switch 112 arrangement illustrated in FIG. 2 configured to dynamically change an impedance of the transmit/receive switch 112, in accordance with an embodiment of the invention. Referring to FIG. 4, the high voltage switch 114 exhibits a fixed resistance. The variable resistor 116 may comprise a plurality of resistors R1-R6 connected in series between the high voltage switch 114 and the low noise amplifier 108 and a plurality of switches T1-T6 for dynamically controlling the amount of resistance provided by the variable resistor 116.

Figure 6:
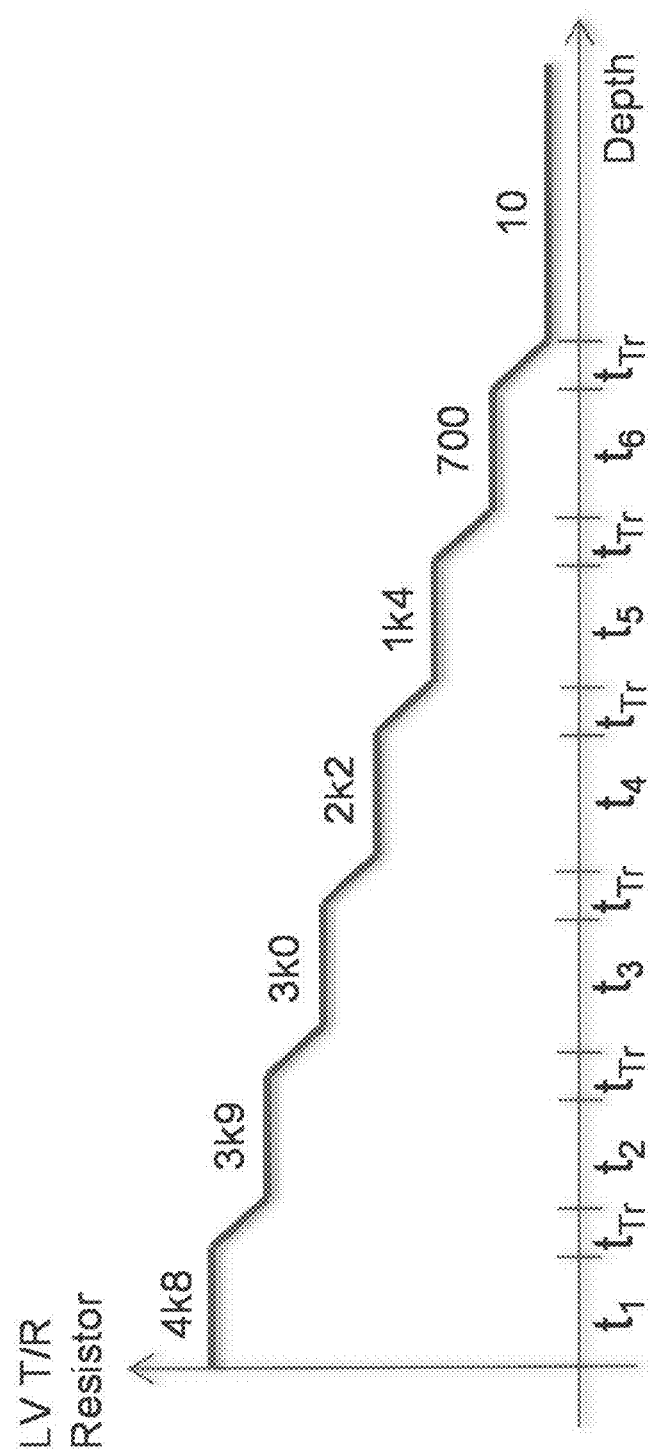
FIG. 6 is a graph illustrating an exemplary resistance of the transmit/receive switch configurations of FIGS. 4 and 5 that are dynamically changed over a depth, in accordance with an embodiment of the invention.

FIG. 6 is a graph illustrating an exemplary resistance of the transmit/receive switch configuration of FIG. 4 that is dynamically changed over a depth, in accordance with an embodiment of the invention. Referring to FIGS. 4 and 6, when the transmit/receive switch 112 is closed at the onset of the receive phase of the ultrasound scan (t1), switches T1-T6 may be open and the resistance provided by the variable resistor may equal R1+R2+R3+R4+R5+R6, which is 4800 ohms in the example of FIGS. 4 and 6. The variable resistor 116 may be dynamically controlled to close switch T1, for example after a pre-determined period of time or based on measured conditions at the transducer 106, providing a resistance equal to R2+R3+R4+R5+R6 after a brief transition period ($t_{Tr}$) caused by the activation of the switch T1, for example. In the example of FIGS. 4 and 6, the resistance provided by the variable resistor may be reduced at time or depth t2 to 3900 ohms. As illustrated in FIG. 6, the resistance of the variable resistor 116 can continue to decrease over time. Referring to FIGS. 4 and 6, the variable resistance can be incrementally decreased by bypassing additional serially-connected resistor(s). For example, closing switch T2 bypasses resistor R2 to provide 3000 ohms resistance at time t3, closing switch T3 bypasses resistor R3 to provide 2200 ohms resistance at time t4, and so on. Switch T6 may provide a nominal amount of resistance, e.g., 10 ohms, when all of switches T1-T6 are closed. In various embodiments, switches T1-T6 may be transistors, or any suitable switching mechanism.

Figure 5:
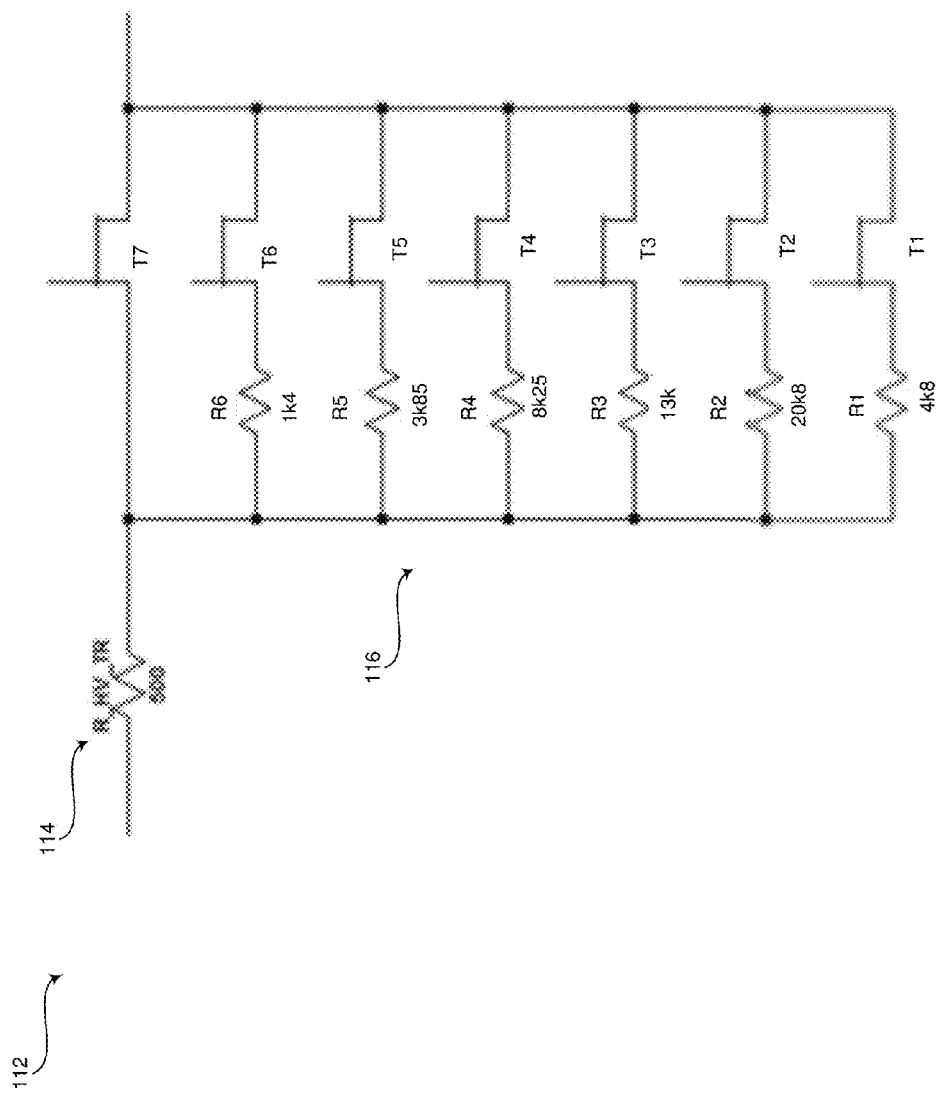
FIG. 5 is a diagram of second exemplary circuitry of the transmit/receive switch arrangement illustrated in FIG. 2 configured to dynamically change an impedance of the transmit/receive switch, in accordance with an embodiment of the invention.

FIG. 5 is a diagram of second exemplary circuitry of the transmit/receive switch 112 arrangement illustrated in FIG. 2 configured to dynamically change an impedance of the transmit/receive switch 112, in accordance with an embodiment of the invention. Referring to FIG. 5, the transmit/receive switch 112 comprises a high voltage switch 114 having a fixed resistance and a variable resistor 116. The variable resistor 116 may be connected in series between the high voltage switch 114 and the low noise amplifier 108. The variable resistor 116 can comprise a plurality of resistors R1-R6, each of the resistors R1-R6 connected in parallel with each other, and a plurality of switches T1-T7 for dynamically controlling the amount of resistance provided by the variable resistor 116.

FIG. 6 is a graph illustrating an exemplary resistance of the transmit/receive switch configuration of FIG. 5 that is dynamically changed over a depth, in accordance with an embodiment of the invention. Referring to FIGS. 5 and 6, when the transmit/receive switch 112 is closed at the onset of the receive phase of the ultrasound scan (t1), switch T1 may be closed and switches T2-T7 may be open such that the resistance provided by the variable resistor may equal R1, which is 4800 ohms in the example of FIGS. 5 and 6. The variable resistor 116 may be dynamically controlled to close switch T2, for example after a pre-determined period of time or based on measured conditions at the transducer 106, providing a resistance equal to (R1*R2)/(R1+R2) after a brief transition period ($t_{Tr}$) caused by the activation of the switch T2, for example. In the example of FIGS. 5 and 6, the resistance provided by the variable resistor may be reduced at time or depth t2 to 3900 ohms. As illustrated in FIG. 6, the resistance of the variable resistor 116 can continue to decrease over time. Referring again to FIGS. 5 and 6, the variable resistance can be incrementally decreased by adding additional resistors in parallel. For example, closing switch T3 provides 3000 ohms resistance at time t3, closing switch T4 provides 2200 ohms resistance at time t4, and so on. Switch T7 may provide a nominal amount of resistance, e.g., 10 ohms, when all of switches T1-T7 are closed. In various embodiments, switches T1-T7 may be transistors, or any suitable switching mechanism.

Referring again to FIG. 2, the low noise amplifier 108 may be operable to amplify the low voltage signals received via the transmit/receive switch 112 during the receive phase while reducing the effect of noise and communicate the amplified signal to the receiver 118. The receiver 118 may be operable to receive and demodulate the signals from the low noise amplifier 108. The demodulated analog signals may be communicated to additional components of the ultrasound system 100 for further processing, storage, and/or display.

The exemplary frontend arrangement of the ultrasound system 100 of FIG. 2 and the first and second exemplary circuitry of the transmit/receive switch 112 of FIGS. 4 and 5 share various characteristics with the exemplary ultrasound system 100 that is operable to dynamically change an impedance of a transmit/receive switch 112 illustrated in FIG. 1 and described above.

Figure 3:
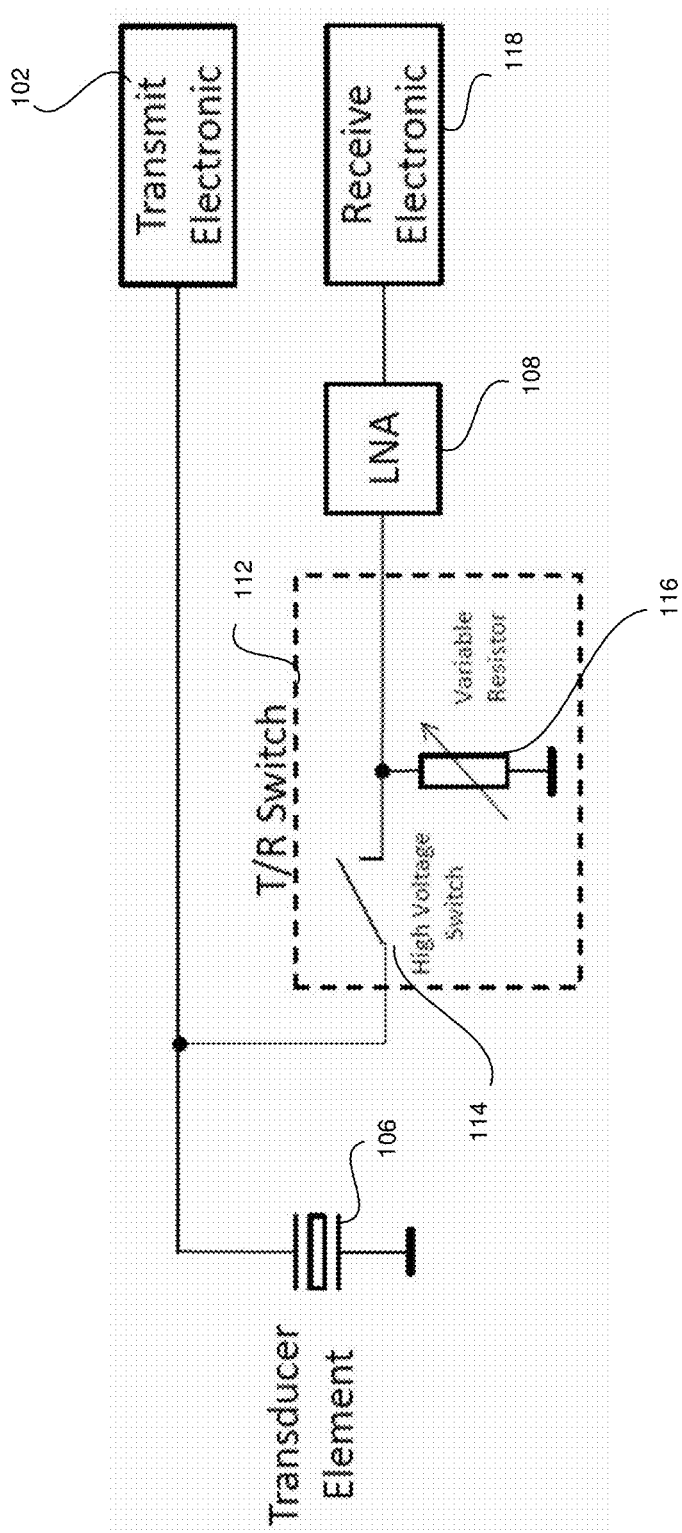
FIG. 3 is a block diagram of an exemplary frontend arrangement of an ultrasound system operable to enhance performance of the ultrasound system by dynamically changing an impedance of a transmit/receive switch, in accordance with an embodiment of the invention.

FIG. 3 is a block diagram of an exemplary frontend arrangement of an ultrasound system operable to enhance performance of the ultrasound system by dynamically changing an impedance of a transmit/receive switch, in accordance with an embodiment of the invention. Referring to FIG. 3, the frontend of the ultrasound system 100 comprises a transmitter 102, a receiver 118, a transducer 106, a transmit/receive switch 112, and a low noise amplifier 108. The transmitter 102 may be operable to drive a group of transducer elements 106 that emit ultrasonic transmit signals into, and receive echoes from, a region of interest. The group of transducer elements 106 in the ultrasound probe 104 may be operable to convert the received echoes into analog signals that are communicated to a receiver 118 by way of a transmit/receive switch 112 and a low noise amplifier 108.

The transmit/receive switch 112 comprises a high voltage switch 114 having a fixed low impedance value and a dynamically controlled variable resistor 116. The variable resistor 116 may be connected after the high voltage switch 114 in parallel between a low noise amplifier 108 and ground. The variable resistor 116 may be configured to change the impedance of the transmit/receive switch 112 over time. For example, to decrease the impedance of the transmit/receive switch 112, the variable part of the transmit/receive switch 112, connected in parallel between a low noise amplifier 108 and ground, would be increased over depth, thereby providing less saturation in the near field and less noise in the far field.

Referring again to FIG. 3, the low noise amplifier 108 may be operable to amplify the low voltage signals received via the transmit/receive switch 112 and communicate the amplified signal to the receiver 118. The receiver 118 may be operable to receive and demodulate the signals from the low noise amplifier 108. The demodulated analog signals may be communicated to additional components of the ultrasound system 100 for further processing, storage, and/or display.

The exemplary frontend arrangement of the ultrasound system 100 of FIG. 3 shares various characteristics with the exemplary ultrasound system 100 that is operable to dynamically change an impedance of a transmit/receive switch 112 illustrated in FIG. 1 and described above.

Figure 7:
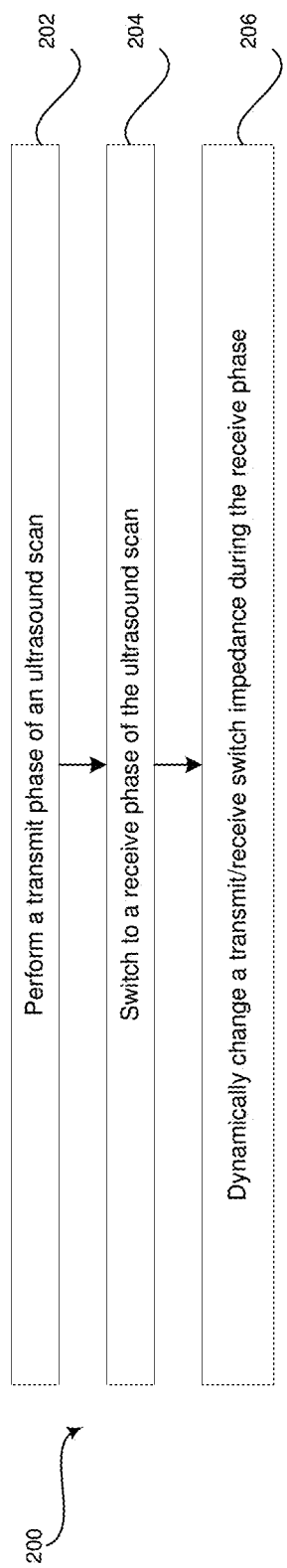
FIG. 7 is a flow chart illustrating exemplary steps that may be utilized for enhancing performance of an ultrasound system by dynamically changing an impedance of a transmit/receive switch, in accordance with an embodiment of the invention.

FIG. 7 is a flow chart 200 illustrating exemplary steps 202-206 that may be utilized for enhancing performance of an ultrasound system 100 by dynamically changing an impedance of a transmit/receive switch 112, in accordance with an embodiment of the invention. Referring to FIG. 7, there is shown a flow chart 200 comprising exemplary steps 202 through 206. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 202, a transmit phase of an ultrasound scan is performed. For example, while transmit/receive switch 112 is open, transmitter 102 may provide a high voltage signal configured to drive the group of transducer elements 106 to emit ultrasonic transmit signals.

In step 204, the ultrasound scan switches from a transmit phase to a receive phase. For example, after the transmitter 102 provides the high voltage signal at step 202, the transmit/receive switch 112 may close to switch to the receive phase of the ultrasonic scan. The transmitted ultrasonic signals may be back-scattered from structures in the object of interest to produce echoes. The echoes are received by the transducer elements 106 and converted into analog signals. The analog signals are provided to receiver 118 after passing through the transmit/receive switch 112, a low noise amplifier 108, and undergoing sub-aperture beamforming. The transmit/receive switch 112 has a high recovery time to ensure that the receiver 118 is able to process the signals communicated by the transducer elements 106, for example, at shallow depths when the transmit time of the acoustic wave beam is short.

The transmit/receive switch 112 is dynamically variable to enhance performance of the ultrasound system 100. When the ultrasound scan switches to the receive phase (i.e., in the near field portion of the receive phase), the receive voltage level may be higher than, for example, during a far field portion of the receive phase. To overcome saturation effects of the low noise amplifier 108 in the near field portion of the receive phase, the transmit/receive switch 112 may be initially set or dynamically adjusted to have a higher impedance, such that the input signal level into the low noise amplifier 108 is reduced. Referring to FIG. 6, for example, the resistance of the variable resistor 116 in the near field, i.e., at t1 to t2, may be at highest resistance settings of the variable resistor 116 when the variable resistor is connected in series between the high voltage switch 114 and the low noise amplifier 108, as illustrated in the exemplary embodiments of FIGS. 2, 4, and/or 5. Additionally and/or alternatively, when the variable resistor is connected after the high voltage switch 114 in parallel between the low noise amplifier 108 and ground, as illustrated in FIG. 3, the resistance of the variable resistor 116 in the near field may be at lowest resistance settings.

In step 206, the transmit/receive switch impedance is dynamically changed during the receive phase. For example, between the near and far fields, i.e., at a depth of a few centimeters between times t3 and t4, reverberation artifacts may be minimized by matching the impedance of the transducer 106 to the impedance of the transmit/receive switch 112 plus the low noise amplifier 108. Minimizing the reverberation artifacts at this depth, for example at the depth of the amniotic fluid in a pregnant uterus, enhances visualization of the amniotic fluid by reducing the reflectivity of the transducer 106. The impedance of the combination of the transmit/receive switch 112 and the low noise amplifier 108 can be matched to the impedance seen at the transducer 106 by, for example, changing the resistance at the variable resistor 116. Referring to FIG. 6, if the impedance seen at the transducer 106 is between 2000-3000 ohms, for example, the resistance of the variable resistor 116 may be dynamically decreased from the t1-t2 levels to the t3-t4 levels by reducing a resistance of the variable resistor 116 when the variable resistor 116 is connected in series between a high voltage switch 114 and an input of a low noise amplifier 108, as illustrated in the exemplary embodiments of FIGS. 2, 4, and/or 5. The switch resistance of the variable part 116 of the transmit/receive switch 112 is independent of the input resistance of the low noise amplifier 108.

As another example, the transmit/receive switch 112 is dynamically variable to enhance performance of the ultrasound system 100 in the far field. Specifically, in the far field, i.e., at t5 and beyond, the impedance of the transmit/receive switch 112 may be adjusted as low as possible to minimize a noise floor of the low noise amplifier 108. Referring to FIG. 6, the resistance of the variable resistor 116 may be dynamically decreased from the t3-t4 levels to the t5-t6 levels by, for example, reducing a number of serially-connected resistors, as illustrated in FIG. 4, or increasing the number of parallel-connected resistors, as illustrated in FIG. 5, when the variable resistor 116 is connected in series, as illustrated in FIGS. 2, 4, and 5. Additionally and/or alternatively, when the variable resistor is connected after the high voltage switch 114 in parallel between the low noise amplifier 108 and ground, as illustrated in FIG. 3, the resistance of the variable resistor 116 in the far field may be increased to highest resistance settings to minimize the noise floor of the low noise amplifier 108. In a representative embodiment, a gain of the low noise amplifier 108 is unaffected by the variable resistance 116 of the transmit/receive switch 112, irrespective of whether the variable resistor 116 is arranged in serial or parallel.

Aspects of the present invention provide a system and method 200 for enhancing performance of an ultrasound system 100 by dynamically changing an impedance of a transmit/receive switch 112. In accordance with various embodiments of the invention, a method 200 comprises closing 204 a transmit/receive switch 112 to provide a receive signal communicated from an ultrasound transducer 106 to a low noise amplifier 108 during a receive phase of an ultrasound scan. The method 200 comprises dynamically adjusting 206 an impedance of the transmit/receive switch 112 while the transmit/receive switch 112 is closed in the receive phase by changing a resistance of the transmit/receive switch 112. In various embodiments, a gain of the low noise amplifier 108 is unaffected by the changing of the resistance of the transmit/receive switch 112.

In a representative embodiment, the method 200 comprises providing 202, by a transmitter 102 before the transmit/receive switch 112 is closed, a transmit signal operable to drive the ultrasound transducer 106 to emit ultrasonic signals. In certain embodiments, the transmit/receive switch 112 comprises a switch 114 having a fixed impedance and a variable resistor 116. In various embodiments, the variable resistor 116 is connected in series between the switch 114 having the fixed impedance and the low noise amplifier 108. In certain embodiments, the variable resistor 116 comprises a plurality of resistors R1-R6 and a plurality of transistors T1-T6. The plurality of resistors R1-R6 is connected in series. The plurality of transistors T1-T6 are configured to one or more of include or bypass one or more of the plurality of resistors R1-R6 to dynamically control the amount of resistance provided by the variable resistor 116. In a representative embodiment, the variable resistor 116 comprises a plurality of resistors R1-R6 and a plurality of transistors T1-T7. Each of the plurality of resistors R1-R6 is connected in parallel with other of the plurality of resistors R1-R6. The plurality of transistors T1-T7 are configured to one or more of include or bypass one or more of the plurality of resistors to dynamically control the amount of resistance provided by the variable resistor 116.

In certain embodiments, the variable resistor 116 is connected after the switch 114 having the fixed impedance in parallel between the low noise amplifier 108 and ground. In a representative embodiment, the receive phase comprises a near field portion, a far field portion, and a portion between the near field and the far field. The resistance of the transmit/receive switch 112 is reduced when going from the near field portion to the portion between the near field and the far field of the receive phase. The resistance of the transmit/receive switch 112 is reduced when going from the portion between the near field and the far field to the far field portion of the receive phase.

In accordance with various embodiments of the invention, a system 100 comprises a transmit/receive switch 112 configured to switch between a transmit phase and a receive phase of an ultrasound scan. The transmit/receive switch 112 provides a receive signal communicated from an ultrasound transducer 106 to a low noise amplifier 108 when in the receive phase. In a representative embodiment, an impedance of the transmit/receive switch 112 is dynamically adjusted by changing a resistance of the transmit/receive switch 112 while the transmit/receive switch 112 is in the receive phase. The low noise amplifier 108 is configured to amplify the receive signal. In certain embodiments, a gain of the low noise amplifier is independent of the resistance of the transmit/receive switch.

In various embodiments, the ultrasound transducer 106 is operable to emit an ultrasonic signal in response to a received transmit signal, receive echoes of the ultrasonic signal, generate the receive signal in response to the received echoes, and communicate the receive signal. In a representative embodiment, the transmit/receive switch 112 comprises a switch 114 having a fixed impedance and a variable resistor 116. In certain embodiments, the switch 114 having the fixed impedance is a high voltage switch.

In a representative embodiment, the variable resistor 116 is connected in series between the switch 114 having the fixed impedance and the low noise amplifier 108. In certain embodiments, the variable resistor 116 comprises a plurality of resistors R1-R6 and a plurality of transistors T1-T6. The plurality of resistors R1-R6 is connected in series. The plurality of transistors T1-T6 are configured to one or more of include or bypass one or more of the plurality of resistors R1-R6 to dynamically control the amount of resistance provided by the variable resistor 116. In various embodiments, the variable resistor 116 comprises a plurality of resistors R1-R6 and a plurality of transistors T1-T7. Each of the plurality of resistors R1-R6 is connected in parallel with other of the plurality of resistors R1-R6. The plurality of transistors T1-T7 are configured to one or more of include or bypass one or more of the plurality of resistors to dynamically control the amount of resistance provided by the variable resistor 116.

In certain embodiments, the receive phase comprises a near field portion, a far field portion, and a portion between the near field and the far field. The resistance of the transmit/receive switch 112 is reduced when going from the near field portion to the portion between the near field and the far field of the receive phase. The resistance of the transmit/receive switch 112 is reduced when going from the portion between the near field and the far field to the far field portion of the receive phase.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing performance of an ultrasound system by dynamically changing an impedance of a transmit/receive switch.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
   closing a transmit/receive switch to provide a receive signal communicated from an ultrasound transducer to a low noise amplifier during a receive phase of an ultrasound scan; and
   dynamically adjusting an impedance of the transmit/receive switch while the transmit/receive switch is closed in the receive phase by changing a resistance of the transmit/receive switch,
   wherein a gain of the low noise amplifier is unaffected by the changing of the resistance of the transmit/receive switch.

2. The method according to claim 1, comprising providing, by a transmitter before the transmit/receive switch is closed, a transmit signal operable to drive the ultrasound transducer to emit ultrasonic signals.

3. The method according to claim 1, wherein the transmit/receive switch comprises a switch having a fixed impedance and a variable resistor.

4. The method according to claim 3, wherein the variable resistor is connected in series between the switch having the fixed impedance and the low noise amplifier.

5. The method according to claim 4, wherein the variable resistor comprises:
   a plurality of resistors connected in series, and
   a plurality of transistors configured to one or more of include or bypass one or more of the plurality of resistors to dynamically control the amount of resistance provided by the variable resistor.

6. The method according to claim 4, wherein the variable resistor comprises:
   a plurality of resistors, each of the plurality of resistors connected in parallel with other of the plurality of resistors, and
   a plurality of transistors configured to one or more of include or bypass one or more of the plurality of resistors to dynamically control the amount of resistance provided by the variable resistor.

7. The method according to claim 3, wherein the variable resistor is connected after the switch having the fixed impedance in parallel between the low noise amplifier and ground.

8. The method according to claim 4, wherein:
   the receive phase comprises a near field portion, a far field portion, and a portion between the near field and the far field,
   the resistance of the transmit/receive switch is reduced when going from the near field portion to the portion between the near field and the far field of the receive phase, and
   the resistance of the transmit/receive switch is reduced when going from the portion between the near field and the far field to the far field portion of the receive phase.

9. A system, comprising:
   a transmit/receive switch configured to switch between a transmit phase and a receive phase of an ultrasound scan, wherein the transmit/receive switch provides a receive signal communicated from an ultrasound transducer to a low noise amplifier when in the receive phase, and wherein an impedance of the transmit/receive switch is dynamically adjusted by changing a resistance of the transmit/receive switch while the transmit/receive switch is in the receive phase; and
   the low noise amplifier configured to amplify the receive signal, wherein a gain of the low noise amplifier is independent of the resistance of the transmit/receive switch.

10. The system according to claim 9, wherein the ultrasound transducer operable to:
    emit an ultrasonic signal in response to a received transmit signal,
    receive echoes of the ultrasonic signal,
    generate the receive signal in response to the received echoes, and
    communicate the receive signal.

11. The system according to claim 9, wherein the transmit/receive switch comprises a switch having a fixed impedance and a variable resistor.

12. The system according to claim 11, wherein the switch having the fixed impedance is a high voltage switch.

13. The system according to claim 11, wherein the variable resistor is connected in series between the switch having the fixed impedance and the low noise amplifier.

14. The system according to claim 13, wherein the variable resistor comprises:
- a plurality of resistors connected in series, and
- a plurality of transistors configured to one or more of include or bypass one or more of the plurality of resistors to dynamically control the amount of resistance provided by the variable resistor.

15. The system according to claim 13, wherein the variable resistor comprises:
- a plurality of resistors, each of the plurality of resistors connected in parallel with other of the plurality of resistors, and
- a plurality of transistors configured to one or more of include or bypass one or more of the plurality of resistors to dynamically control the amount of resistance provided by the variable resistor.

16. The system according to claim 11, wherein the variable resistor is connected after the switch having the fixed impedance in parallel between the low noise amplifier and ground.

17. The system according to claim 13, wherein:
- the receive phase comprises a near field portion, a far field portion, and a portion between the near field and the far field,
- the resistance of the transmit/receive switch is reduced when going from the near field portion to the portion between the near field and the far field of the receive phase, and
- the resistance of the transmit/receive switch is reduced when going from the portion between the near field and the far field to the far field portion of the receive phase.

18. A non-transitory computer readable medium having stored thereon, a computer program having at least one code section, the at least one code section being executable by a machine for causing the machine to perform steps comprising:
- closing a transmit/receive switch to provide a receive signal communicated from an ultrasound transducer to a low noise amplifier during a receive phase of an ultrasound scan; and
- dynamically adjusting an impedance of the transmit/receive switch while the transmit/receive switch is closed in the receive phase by changing a resistance of the transmit/receive switch, wherein a gain of the low noise amplifier is unaffected by the changing of the resistance of the transmit/receive switch.

19. The non-transitory computer readable medium according to claim 18, providing before the transmit/receive switch is closed, a transmit signal operable to drive a transducer to emit ultrasonic signals.

20. The non-transitory computer readable medium according to claim 18, wherein:
- the receive phase comprises a near field portion, a far field portion, and a portion between the near field and the far field,
- the resistance of the transmit/receive switch is reduced when going from the near field portion to the portion between the near field and the far field of the receive phase, and
- the resistance of the transmit/receive switch is reduced when going from the portion between the near field and the far field to the far field portion of the receive phase.

* * * * *